US009261469B2

(12) United States Patent  (10) Patent No.: US 9,261,469 B2
Selim  (45) Date of Patent: Feb. 16, 2016

(54) LUMINESCENCE BASED SPECTROMETERS

(71) Applicant: Farida A. Selim, Pullman, WA (US)

(72) Inventor: Farida A. Selim, Pullman, WA (US)

(*) Notice: Subject to any disclaimer, the term of this patent is extended or adjusted under 35 U.S.C. 154(b) by 0 days.

(21) Appl. No.: 14/198,930

(22) Filed: Mar. 6, 2014

(65) Prior Publication Data
US 2014/0254752 A1   Sep. 11, 2014

Related U.S. Application Data

(60) Provisional application No. 61/774,189, filed on Mar. 7, 2013.

(51) Int. Cl.
*G01T 1/10* (2006.01)
*G01N 23/223* (2006.01)

(52) U.S. Cl.
CPC ........ *G01N 23/223* (2013.01); *G01N 2223/076* (2013.01)

(58) Field of Classification Search
CPC .......... G01N 21/6428; G01N 21/6458; G01N 2021/7786; G01N 21/648; G01N 23/223; G01N 2223/076
USPC .................................................... 250/361 R
See application file for complete search history.

(56) References Cited

U.S. PATENT DOCUMENTS

| 5,042,494 | A * | 8/1991 | Alfano | 600/477 |
| 5,754,620 | A * | 5/1998 | Hossain et al. | 378/45 |
| 6,753,957 | B1 * | 6/2004 | Graft et al. | 356/318 |
| 2003/0062463 | A1 * | 4/2003 | Narita et al. | 250/201.3 |
| 2004/0150818 | A1 * | 8/2004 | Armstrong et al. | 356/301 |
| 2007/0063154 | A1 * | 3/2007 | Chen et al. | 250/483.1 |
| 2008/0116272 | A1 * | 5/2008 | Giering et al. | 235/439 |
| 2010/0016783 | A1 * | 1/2010 | Bourke et al. | 604/20 |
| 2011/0022328 | A1 * | 1/2011 | Granot et al. | 702/19 |
| 2013/0193346 | A1 * | 8/2013 | Justel et al. | 250/459.1 |

OTHER PUBLICATIONS

Author: C. R. Varney et al., Title: X-ray luminescence based spectrometer for investigation of scintillation properties, Date: Oct. 31, 2012, Publisher: Review of Scientific Instruments.*
Author: L. Armelao et al., Title: X-ray Excited Optical Luminescence Studies of ZnO and Eu-Doped ZnO Nanostructures, Date: Apr. 26, 2007, Publisher: J. Phys. Chem. C.*
S. R. Rotman and C. Warde, J. Appl. Phys. 58, 522 (1985).
C. Eijk, Nuclear Instruments and Methods in Physics Research A 392, 285 (1997).
S. Kubota, et al., Nucl. Instr. And Meth. A 268, 275 (1997).
B. Li, et al., Mat. Res. Bull. 35, 1921 (2000).

(Continued)

*Primary Examiner* — David J Makiya
*Assistant Examiner* — Taeho Jo
(74) *Attorney, Agent, or Firm* — Marshall & Melhorn, LLC

(57) ABSTRACT

Various embodiments of systems, components, modules, routines, and processes for luminescence based spectral measurement are described herein. In one embodiment, a method for measuring a scintillation property of a sample includes directing an ionizing radiation toward the sample, thereby inducing the sample to produce an emission. The method also includes acquiring a spectral luminescence of the produced emission by the sample, the spectral luminescence including a plurality of luminescence intensities at corresponding emission wavelengths or frequencies. The scintillation property of the sample may then be determined based on the acquired spectral luminescence.

20 Claims, 4 Drawing Sheets

(56) References Cited

OTHER PUBLICATIONS

K.G. Rajan and A.J. Lanus, Pramana—J. Phys., 65, 323 (2005).
A. Baciero, et al., J. Appl. Phys. 85, 6790 (1999).
D. Cavouras, et al., App. Phys. B 80, 923 (2005).
S. L. David, et al., IEEE Nucl. Sci. Symp. Conf. Rec. M06, 3950 (2008).
S. L. David, et al., e-JST, 2, 63 (2010).
I. Kandarakis, et al., Nucl. Instr. and Meth. In Phys. Res. A 538, 615 (2005).
V. Pankratov, et al., Radiat. Meas. 42, 679 (2007).
V. Babin, et al., Phys. Stat. Sol. (c) 2, 97 (2005).
Y. Zorenko, et al., Radiat. Meas. 45, 389 (2010).
M. K. Ashurov, et al., Sol. St. Comm. 120, 491(2001).
C. R. Varney, et al., AIP Advances 1, 042170 (2011).
Y. Suzuki, et al., Mat. Sci. For. 239-241, 219 (1997).
E. Zych, et al., J. Phys.: Condens.. Matter 12, 1947 (2000).
C. R. Varney, et al., J. Phys. D.: Appl. Phys. 45, 1 (2012).

* cited by examiner

LUMINESCENCE BASED SPECTROMETERS

CROSS-REFERENCE TO RELATED APPLICATION(S)

This application is a Non-provisional Application of U.S. Provisional Application No. 61/774,189, filed on Mar. 7, 2013.

BACKGROUND

Photoluminescence tests or scintillation measurements have been used to study potential scintillation materials. During photoluminescence tests, a scintillation material is illuminated by a source light with a predetermined frequency or frequency range. In response, the scintillation material produce a luminescence, which can then be recorded for studying emission efficiency of luminescence centers and spectral ranges of the scintillation material. However, photoluminescence tests do not provide information regarding efficiencies of charge carriers generation, presence of trapping defects, or efficiency of energy transfer from charge carriers to luminescence centers in the scintillation material. On the other hand, scintillation measurements involve coupling a scintillator to a light sensor, (e.g., a photomultiplier tube or photodiode), to measure intensity of luminescence emitted from the scintillation material. Such scintillation measurements do not provide a spectral range or emission efficiency of the scintillation material.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present technology is directed to luminescence based spectrometers and related methods useful for measuring properties of scintillation or other luminescence materials by using x-ray or other suitable ionizing radiation as an excitation source and recording the luminescence spectra as a function of wavelength. The recorded luminescence spectra can then be analyzed to determine most if not all luminescence centers and to allow inspection of emission efficiencies of the scintillation material. The recorded luminescence spectra can also provide information about efficiencies of charge carrier production and energy transfer to luminescence centers in the scintillation material. As a result, both defects responsible for charge-carrier trapping and defects responsible for worsening timing resolution may be identified.

BRIEF DESCRIPTION OF THE DRAWINGS

In FIGS. 3a and 3b, the samples were grown in a mixed atmosphere of argon and hydrogen with 0.15% atmosphere Ce, and the samples were grown in a pure argon atmosphere have 0.3% atmosphere Ce, respectively.

Annealing was carried out in air at 1200° C. for 48 hours. The spectra were recorded using (a) 20 second integration and (b) 65 second integration.

Figure 4A:
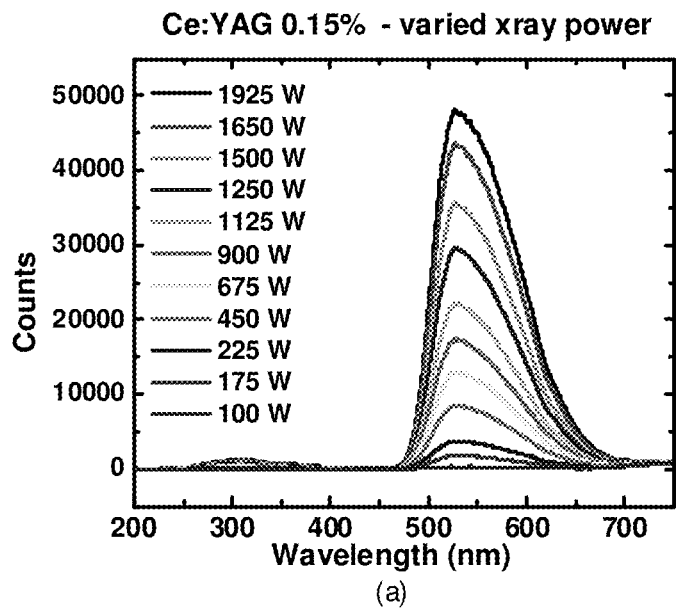

FIG. 4A shows an example luminescence spectra at various x-ray powers.

Figure 4B:
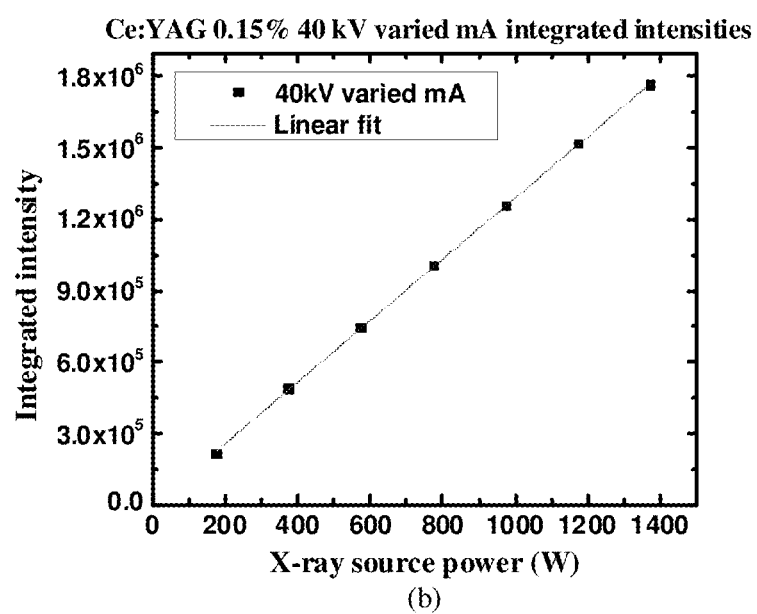

FIG. 4B shows an example light yield calculated by taking the integrated 530 nm peak versus x-ray power, for Ce (0.15%) doped YAG.

Figure 5:
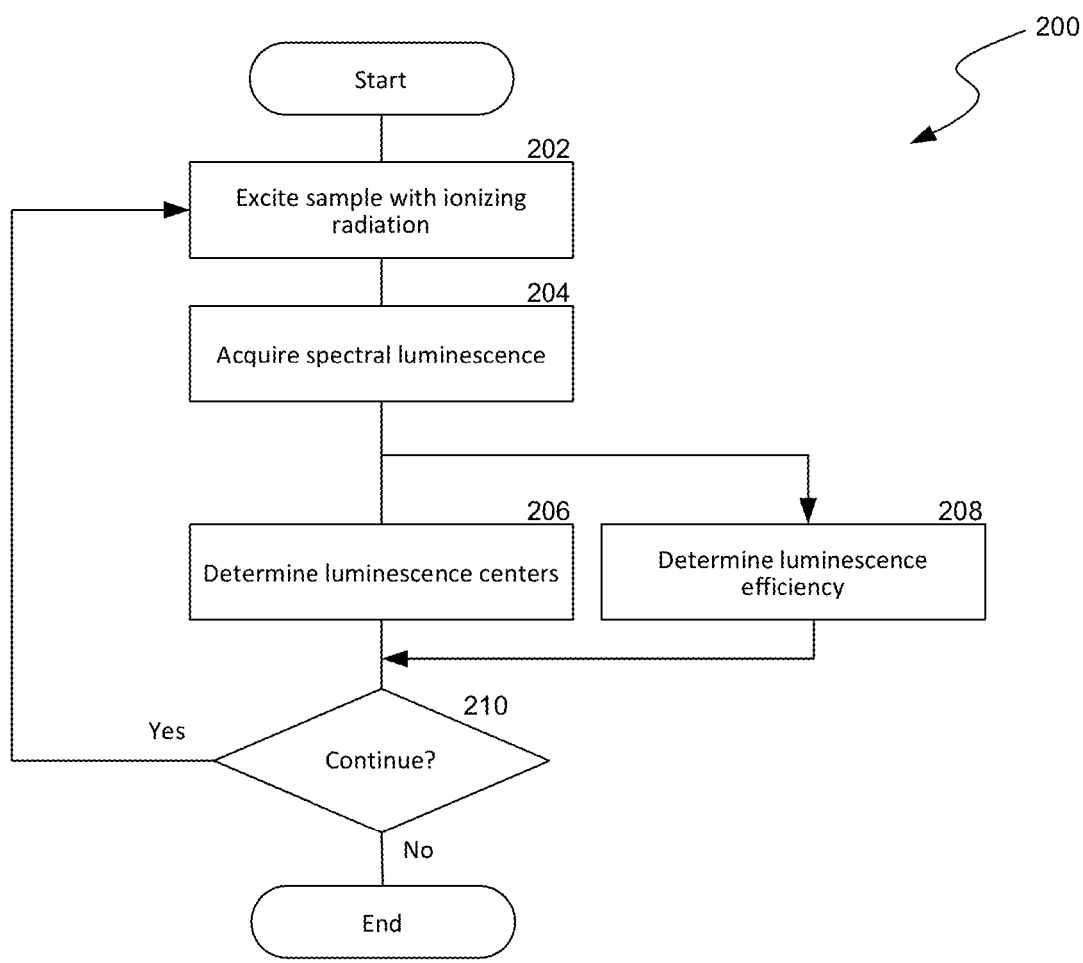

FIG. 5 is flowchart illustrating a process of luminescence based spectral measurement in accordance with embodiments of the present technology.

DETAILED DESCRIPTION

Various embodiments of systems, components, modules, routines, and processes for luminescence based spectral measurement are described below. Certain example systems, devices, and methods are described below with particular components and operations for illustration purposes only. Other embodiments in accordance with the present technology may also include other suitable components and/or may operate at other suitable conditions. A person skilled in the relevant art will also understand that the technology may have additional embodiments, and that the technology may be practiced without several of the details of the embodiments described below with reference to FIGS. 1-5.

As discussed above, neither photoluminescence tests nor scintillation measurements are efficient and effective to measure scintillation efficiency and/or other luminescence characteristics of scintillation materials, fluorescence materials, or luminescence materials in general. It is introduced in this disclosure that x-ray induced luminescence can be utilized as an efficient and effective technique to determine scintillation properties of luminescence materials while simultaneously gaining information about the efficiency of charge carrier production and energy transfer from charge carriers to luminescence centers.

Certain aspects of the present technology are directed to a spectrometer that allows one to efficiently determine scintillation properties of a sample by using x-ray, Y-ray, or other suitable ionizing radiation as an excitation source and acquire emission spectra from the sample in response to the excitation. In the following description, luminescence spectra and scintillation properties of un-doped and Ce doped YAG single crystals were studied for illustration purposes. In other embodiments, aspects of the present invention may be applied for determining other suitable scintillation properties of other suitable luminescence materials.

Without being bound by theory, it is believed that x-ray may interact with lattice atoms of a sample (e.g., YAG) and induce luminescence as follows: absorption of x-ray in the lattice produces electron-hole pairs, which can then be captured by luminescence centers leading to emission. Alternatively, the electron-hole pairs or other charge carriers can be trapped by lattice defects and/or can decay by non-radiative processes producing, for example, heat instead of luminescence.

Figure 1:
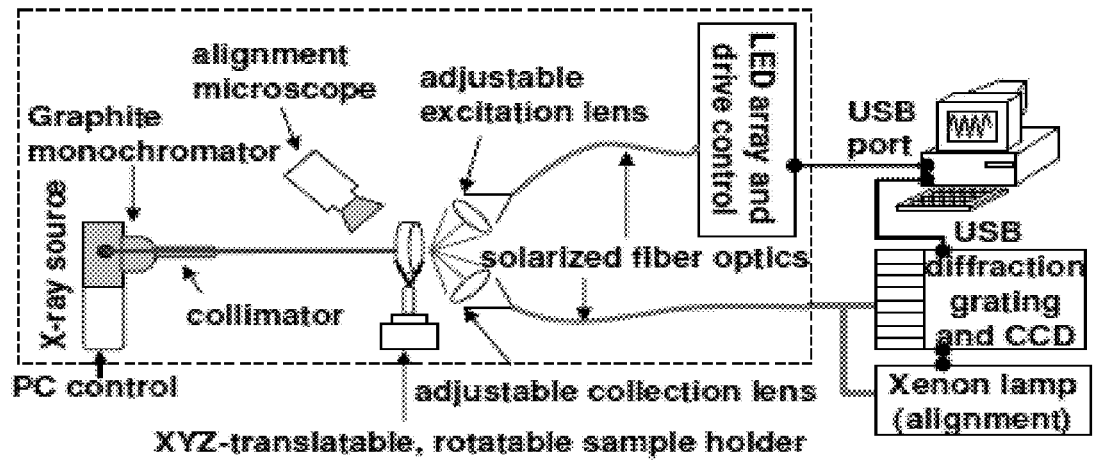
FIG. 1 is a schematic diagram illustrating an example spectrometer based on x-ray luminescence in accordance with embodiments of the present technology.

FIG. 1 shows a schematic diagram of an example spectrometer based on x-ray luminescence in accordance with embodiments of the present technology. Even though particular components for generating x-ray luminescence are shown in FIG. 1, in other embodiments, the spectrometer may include additional and/or different components. In further embodiments, the spectrometer can also include components for generating Y-ray, neutron ray, and/or other suitable ionizing radiation.

As shown in FIG. 1, an excitation source (e.g., Cu x-ray tube AEG FK 60-04) may be used to generate an ionizing radiation (e.g., x-ray beams) that pass through an optional mono-chromator and collimator to obtain focused x-ray beams. A sample station that permits translational motion in x, y, and z directions and 180° rotation is located to receive the focused x-ray beams. The sample holder can be adjusted to allow measurements of both single crystals and powders. The light emitted from the sample is collected and focused through a lens on an optical fiber that transmits the light to a spectral emission detector (e.g., an Ocean Optics USB2000+ spectro-fluorometer that covers a spectral range from 200-800 nm with 1 nm resolution). A light source (e.g., Ocean Optics PX-2 Pulsed Xenon Light Source) may be connected to align the collection lens with the x-ray beam on the sample.

The spectrometer may also be configured to perform photoluminescence measurements with a light source for excitation. For example, the excitation light source may include a light source such as an LED light source array (e.g., Sandhouse Design multi-channel LED) with variable wavelengths or a wide spectrum source with monochromator to provide excitation light to the sample through another fiber optics and lens. The spectrometer and the light source can be operated by a computer (e.g., a PC system having a processor and a memory). The processor can include a mainframe processor, a microprocessor, a field-programmable gate array, and/or other suitable logic devices. The memory can include volatile and/or nonvolatile computer readable storage media (e.g., magnetic disk storage media, optical storage media, and flash memory drives) excluding propagating signals. The x-ray source, sample station, lenses, optical fibers, and light source may be inside a radiation-safe chamber with adequate shielding to absorb x rays and prevent any stray light from outside reaching the sample or lenses. The example Cu x-ray tube may be operated using a commercial x-ray generator that allows the adjustment of the operating voltage and current and provides power up to 2 kW.

Even though a particular excitation source is described above for providing an ionizing radiation, in other embodiments, the spectrometer may include a pulsed radiation source (e.g., a pulsed x-ray source) instead of or in addition to a steady or continuous excitation source, a pulsed laser, and/or a pulsed light source for excitation. Such arrangements can allow synchronization of the different mechanisms (e.g., x-ray with light excitation) and perform photo-luminescence measurements during, for example, x-ray pulses. It is believed that such a synchronization can be a powerful technique to study a variety of molecular, atomic, electronic and optical properties. It is also believed that the spectrometer with such features can be a valuable tool for a wide range of materials in photonic, semiconductor, electronic, sensor, detection, imaging, biology and life science.

Several tests were conducted using the spectrometer of FIG. 1. Samples studied included single crystals of YAG un-doped or doped with Ce impurities that were separately grown by the Czochralski method under: (1) a reducing atmosphere of 40% hydrogen in argon, (2) a modestly oxidizing atmosphere of 100 ppm oxygen in nitrogen, or (3) a nonreactive atmosphere of argon. Sample sizes were either 5×5×1 mm or 10 mm dia.×1 mm. After growth, some samples were annealed in air at 1200° C. The spectra were recorded under the excitation of collimated and mono-chromated x-ray beams. The setting of the x-ray tube in most measurements was 45 kV and 25 mA. All measurements were performed at room temperature.

Figure 2:
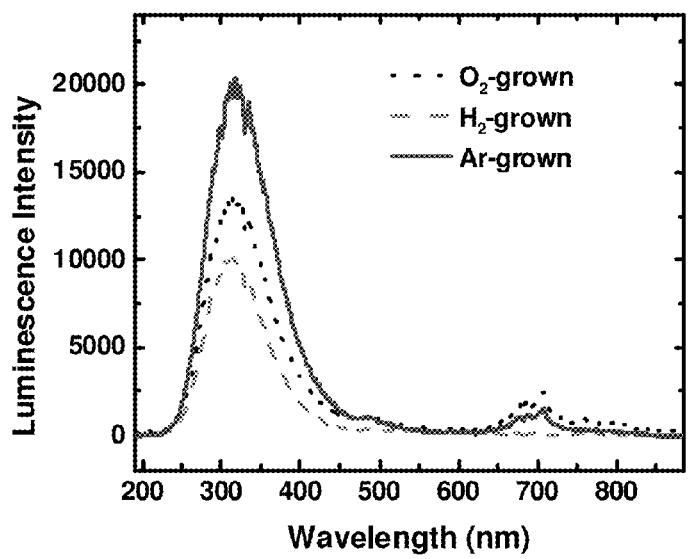
FIG. 2 is an example x-ray luminescence spectra of a number of un-doped yttrium aluminum garnet ($Y_3Al_5O_{12}$, YAG) samples grown under different atmospheres.

FIG. 2 shows the emission spectra of a number of un-doped YAG samples under x-ray excitation. By inspecting the spectra one can identify most or even all the luminescence centers in un-doped YAG. Such information may not be available if using photoluminescence spectroscopy due to requirements of selecting the correct excitation wavelength(s). As shown in FIG. 2, a peak exists at 320 nm that may be attributed to self-trapped excitons and $Y_{Al}^{3+}$ antisite defects (ADs). The peak is stronger for the samples grown in Argon atmosphere which suggests an increase in AD density over other samples. The spectra in FIG. 2 has a shoulder to the 320 nm peak around 500 nm. The peak at 700 nm is believed as due to $Fe^{3+}$ trace impurities.

Figure 3A:
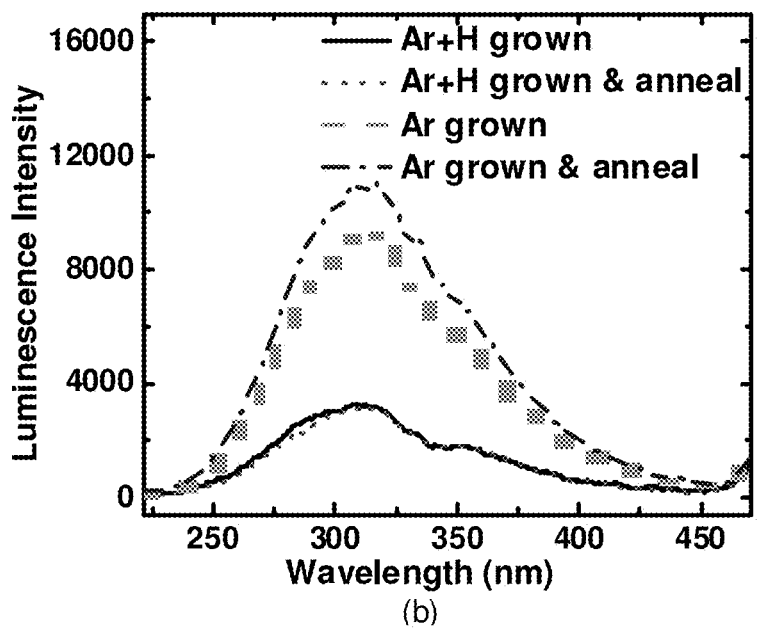
FIGS. 3A and 3B are example x-ray luminescence spectra of Ce-doped YAG samples of certain growth environment and post-growth treatments.

FIGS. 3A and 3A show x-ray induced luminescence spectra of as-grown and annealed Ce:YAG samples, respectively. As with the un-doped YAG, one can observe the 320 nm emission associated with $Y_{Al}^{3+}$ ADs, in addition to a strong peak at 530 nm. This strong peak is believed to be a result of the $5d_1$-4f transition of $Ce^{3+}$. It can be seen from FIG. 3A that annealing the $H_2$+Ar-grown Ce:YAG sample in air resulted in a large increase in $Ce^{3+}$ luminescence. A possible cause is that annealing in air may lead to a reduction in the number of oxygen vacancies that trap charge carriers and prevent them from reaching Ce ions.

The spectrometer as shown in FIG. 1 allows simultaneously photoluminescence measurements on the samples, which showed generally no change in the photoluminescence emission intensity after annealing. Thus, it is believed that the improvement in x-ray luminescence is a result of suppressing trapping defects as discussed above. Such detailed information about influence of trapping defects on energy transfer to luminescence centers may not be obtained by standard scintillation measurements or photoluminescence tests.

Figure 3B:
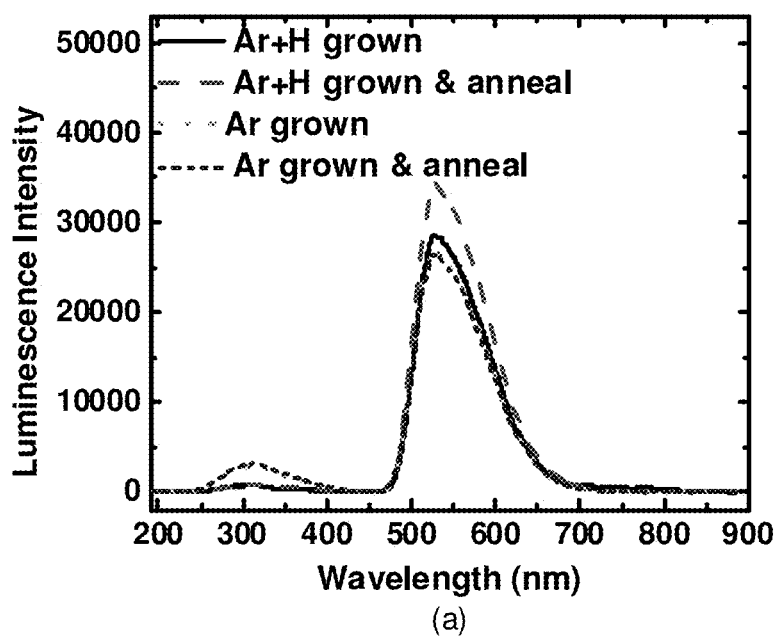

The x-ray luminescence spectra in FIG. 3B for Ce:YAG samples were recorded with larger integration time to examine AD 320 nm peak in Ce:YAG. The peak has a dip at 340 nm which is consistent with an absorption band at 340 nm in Ce:YAG corresponding to a transition in $Ce^{3+}$ between $4d$-$5f_2$ levels. The dip seems to be more pronounced in the samples grown in argon and hydrogen. In absorption measurements, the samples grown in argon and hydrogen show stronger absorption than the samples grown in argon only, which appear to agree with behavior of the 320 nm peak in the x-ray luminescence measurements.

These features in the 320 nm peak indicate that a number of charge carriers transfer their energy to the AD centers that emit UV luminescence (320 nm). This UV luminescence then participates in $Ce^{3+}$ excitation. This subsequent absorption and emission may have significant effects on the time decay of the scintillation signals of Ce:YAG crystals. It has been predicted that a transfer of energy from defects to Ce centers may take place in Ce:YAG crystals. It has also been suggested that this radiative transfer of energy may significantly increase the decay time of the 530 nm emission and delay the scintillation process.

The energy resolution of a scintillation detector may be characterized by proportionality of a material response and how a light yield increases with increasing energy deposition in the lattice. The proportional increase of emission with increasing x-ray power in FIG. 4A and the linearity in FIG. 4B are indication for the possibility of achieving very high energy resolution for Ce:YAG detectors.

FIG. 5 is flowchart illustrating a process 200 of luminescence based spectral measurement in accordance with embodiments of the present technology. As shown in FIG. 5, the process 200 can include exciting a sample with an ionizing radiation (e.g., x-ray) at stage 202. In response to the excitation, the sample emits luminescence. The process 200 then includes capturing and acquiring spectral luminance of the sample at stage 204. Examples of such spectral luminance are shown in FIGS. 2, 3A, and 3B.

The process 200 can then include analyzing the acquired spectral luminance to determine luminescence centers with corresponding emission frequencies at stage 206 and determining a luminescence efficiency at stage 208. In one embodiment, the luminescence efficiency may be determined by comparing a power of an excitation source that produces the ionizing radiation and an intensity of the acquired luminescence. In another embodiment, a relationship between the power of an excitation source and the intensity of the acquired luminescence may also be determined. The process 200 then includes a decision stage 210 to determine if the process continues. If the process continues, the process 200 reverts to exciting the sample at stage 202; otherwise, the process ends.

In addition to revealing all luminescence centers in the crystals and their interaction with defects, the new spectrometer can provide information about the linearity and proportionality of the material response to radiation, which are important characteristics for the scintillation material that defines its energy resolution. This was studied for Ce:YAG crystals by changing the x-ray power and recording the luminescence. FIG. 4(a) shows the rise of Ce emission by increasing the power of x-ray tube while FIG. 4(b) presents the integrated intensity versus x-ray power and indicates excellent linearity, confirming the possibility of achieving high energy resolution.

Specific embodiments of the technology have been described above for purposes of illustration. However, various modifications may be made without deviating from the foregoing disclosure. In addition, many of the elements of one embodiment may be combined with other embodiments in addition to or in lieu of the elements of the other embodiments. Accordingly, the technology is not limited except as by the appended claims.

I claim:

1. A method for determining a scintillation property of a sample, the method comprising: directing an ionizing radiation toward the sample, thereby inducing the sample to produce an emission; acquiring a spectral luminescence of the produced emission by the sample, the spectral luminescence including a plurality of luminescence intensities at corresponding emission wavelengths or frequencies; analyzing the acquired spectral luminescence to determine the following: defects responsible for charge-carrier trapping and/or defects responsible for worsening timing resolution, and thereby determining the scintillation property of the sample based on the acquired spectral luminescence.

2. The method of claim 1 wherein:
directing an ionizing radiation includes directing an x-ray beam toward the sample; and
determining the scintillation property includes determining one or more luminescence centers of the sample.

3. The method of claim 1 wherein:
directing an ionizing radiation includes directing an x-ray beam toward the sample; and
determining the scintillation property includes determining one or more luminescence centers of the sample by identifying a local maximum intensity in the acquired spectral luminescence.

4. The method of claim 1 wherein:
directing an ionizing radiation includes directing an x-ray beam toward the sample; and
determining the scintillation property includes determining a luminescence efficiency of the sample.

5. The method of claim 1 wherein:
the method further includes producing the ionizing radiation using an excitation source; and
determining the scintillation property includes determining a relationship between a power of the excitation source and an integrated intensity of the acquired spectral luminescence.

6. The method of claim 1 wherein:
the method further includes producing the ionizing radiation using an excitation source; and
determining the scintillation property includes determining a relationship between a power of the excitation source and an integrated intensity of the acquired spectral luminescence, the relationship being linear.

7. A spectrometer, comprising:
an excitation source configured to direct an ionizing radiation toward a sample, thereby inducing the sample to produce an emission; an emission detector configured to acquire a spectral luminescence of the produced emission by the sample, the spectral luminescence including a plurality of luminescence intensities at corresponding emission wavelengths or frequencies; a collimator to collimate the x-ray beam and measuring luminescence and scintillation properties with microns spatial resolution and scanning the luminescence and scintillation across samples; and a XYZ-translatable, rotatable sample holder to enhance scanning capabilities; and a computer configured to receive the acquired spectral luminescence to determine the following:
defects responsible for charge-carrier trapping and/or defects responsible for worsening timing resolution, and thereby determine the scintillation property of the sample based on the acquired spectral luminescence.

8. The spectrometer of claim 7 wherein:
the excitation source includes an x-ray source; and
the scintillation property includes one or more luminescence centers of the sample.

9. The spectrometer of claim 7 wherein:
the excitation source includes an x-ray source; and
the scintillation property includes one or more luminescence centers of the sample individually identified by a local maximum intensity in the acquired spectral luminescence.

10. The spectrometer of claim 7 wherein:
the excitation source includes an x-ray source; and
the scintillation property includes a luminescence efficiency of the sample.

11. The spectrometer of claim 7 wherein:
the excitation source includes an x-ray source; and
the scintillation property includes a relationship between a power of the excitation source and an integrated intensity of the acquired spectral luminescence.

12. The spectrometer of claim 11 can test the linearity of the sample response to ionizing radiation and predict the energy resolution of the material as a detector.

13. A computer system programmed to determine a scintillation property of a sample, the computer system having a processor and a memory containing instructions, when executed by the processor, causing the process to perform a method comprising: directing the excitation source to supply an ionizing radiation toward a sample, thereby inducing the sample to produce an emission; directing the emission detector to acquire a spectral luminescence of the produced emission by the sample, the spectral luminescence including a plurality of luminescence intensities at corresponding emission wavelengths or frequencies; receiving the acquired spectral luminescence from the emission detector; analyzing the acquired spectral luminescence to determine the following: defects responsible for charge-carrier trapping and/or defects responsible for worsening timing resolution, and thereby determining the scintillation property of the sample based on the acquired spectral luminescence.

14. The computer system of claim 13 wherein:
the excitation source includes an x-ray source; and
determining the scintillation property includes determining one or more luminescence centers of the sample.

15. The computer system of claim 13 wherein:
the excitation source includes an x-ray source; and
determining the scintillation property includes determining one or more luminescence centers of the sample by identifying a local maximum intensity in the acquired spectral luminescence.

16. The computer system of claim 13 wherein:
the excitation source includes an x-ray source; and
determining the scintillation property includes determining a luminescence efficiency of the sample.

17. The computer system of claim 13 wherein determining the scintillation property includes determining a relationship between a power of the excitation source and an integrated intensity of the acquired spectral luminescence.

18. The computer system of claim 13 wherein determining the scintillation property includes determining a relationship between a power of the excitation source and an integrated intensity of the acquired spectral luminescence, the relationship being linear.

19. The computer system of claim 13 wherein:
the excitation source includes a continuous x-ray source; and
determining the scintillation property includes determining a luminescence efficiency of the sample.

20. The computer system of claim 13 wherein:
the excitation source includes a pulsed x-ray source; synchronized with pulsed light emitting diodes or pulsed light sources and measuring photoluminescence during x-ray excitation and determining the luminescence properties when the atoms are in excited states.

* * * * *